(12) United States Patent
Ahmad et al.

(10) Patent No.: US 9,833,584 B2
(45) Date of Patent: Dec. 5, 2017

(54) PORTABLE VENTILATOR SECRETION MANAGEMENT SYSTEM

(71) Applicant: Breathe Technologies, Inc., Irvine, CA (US)

(72) Inventors: Samir S. Ahmad, San Diego, CA (US); Leonardo Alberto Baloa Welzien, Lake Forest, CA (US)

(73) Assignee: Breathe Technologies, Inc., Irvine, CA (US)

( * ) Notice: Subject to any disclaimer, the term of this patent is extended or adjusted under 35 U.S.C. 154(b) by 243 days.

(21) Appl. No.: 13/849,443

(22) Filed: Mar. 22, 2013

(65) Prior Publication Data

US 2014/0283834 A1 Sep. 25, 2014

(51) Int. Cl.
*A61M 16/00* (2006.01)
*A61M 16/06* (2006.01)
(Continued)

(52) U.S. Cl.
CPC ........ *A61M 16/0069* (2014.02); *A61M 16/00* (2013.01); *A61M 16/0051* (2013.01); *A61M 16/06* (2013.01); *A61M 16/101* (2014.02); *A61M 16/107* (2014.02); *A61M 16/202* (2014.02); *A61M 2016/0027* (2013.01); *A61M 2016/0033* (2013.01); *A61M 2202/0208* (2013.01);
(Continued)

(58) Field of Classification Search
None
See application file for complete search history.

(56) References Cited

U.S. PATENT DOCUMENTS 4,527,557 A * 7/1985 DeVries ................ A61M 16/00
128/204.23
4,838,257 A * 6/1989 Hatch .................. A61M 16/00
128/204.18
(Continued)

FOREIGN PATENT DOCUMENTS

WO WO 2012056373 A1 * 5/2012 ............ A61M 16/00

OTHER PUBLICATIONS

National Jewish Health, "Spirometry Testing (Lung Function Testing)", retrieved from https://web.archive.org/web/20120514234324/http://www.nationaljewish.org/programs/tests/pulmonary-physiology/pulmonary-function/spirometry/ with date May 14, 2012.*
(Continued)

*Primary Examiner* — (Jackie) Tan-Uyen T Ho
*Assistant Examiner* — Joseph D Boecker
(74) *Attorney, Agent, or Firm* — Stetina Brunda Garred and Brucker; Mark B. Garred (57) ABSTRACT

A patient ventilator secretion management system is disclosed. The system has a valve with an input in pneumatic communication with a therapeutic breathing gas source. The valve has variable positions, each of which corresponds to a specific flow rate of gas being output therefrom. A patient ventilation interface is in pneumatic communication with the valve over a gas delivery circuit. A controller in communication with the valve regulates the position thereof. The controller sequentially switches the valve from one of the variable positions to another to output a first range of fluctuating flow rates of gas for delivery to the patient ventilation interface during at least a selected one of patient expiratory and inspiratory phases.

21 Claims, 9 Drawing Sheets

(51) Int. Cl.
*A61M 16/08* (2006.01)
*A61M 16/20* (2006.01)
*A61M 16/10* (2006.01)

(52) U.S. Cl.
CPC ... *A61M 2205/50* (2013.01); *A61M 2205/505* (2013.01); *A61M 2205/8206* (2013.01)

(56) References Cited

U.S. PATENT DOCUMENTS

| | | | |
|---|---|---|---|
| 5,116,088 A * | 5/1992 | Bird | A61M 16/00 128/202.27 |
| 5,611,335 A | 3/1997 | Makhoul | |
| 5,692,497 A * | 12/1997 | Schnitzer | A61M 16/00 128/204.18 |
| 5,694,923 A * | 12/1997 | Hete | A61M 16/00 128/204.18 |
| 5,704,346 A | 1/1998 | Inoue | |
| 5,862,802 A * | 1/1999 | Bird | 128/204.18 |
| 6,085,746 A | 7/2000 | Fox | |
| 6,176,235 B1 | 1/2001 | Benarrouch | A61F 11/00 128/200.24 |
| 6,257,234 B1 * | 7/2001 | Sun | A61M 16/0051 128/204.18 |
| 6,415,791 B1 | 7/2002 | Van Brunt | |
| 6,557,554 B1 | 5/2003 | Sugiura | |
| 6,581,596 B1 | 6/2003 | Truitt et al. | |
| 6,595,213 B2 | 7/2003 | Bennarsten | |
| 6,708,690 B1 * | 3/2004 | Hete | A61M 16/0096 128/204.18 |
| 7,165,547 B2 | 1/2007 | Truitt et al. | |
| 7,168,429 B2 | 1/2007 | Matthews et al. | |
| 7,478,634 B2 | 1/2009 | Jam | |
| 7,770,580 B2 | 8/2010 | Krüger et al. | |
| 7,779,841 B2 | 8/2010 | Dunsmore et al. | |
| 7,861,716 B2 | 1/2011 | Borrello | |
| 8,051,854 B2 | 11/2011 | Faram | |
| 8,230,857 B2 | 7/2012 | Cewers | |
| 8,365,727 B2 | 2/2013 | Dunsmore et al. | |
| 8,539,952 B2 * | 9/2013 | Carbone | A61M 16/20 128/204.21 |
| 2003/0192545 A1 * | 10/2003 | Truitt | A61M 16/0006 128/204.18 |
| 2007/0006924 A1 * | 1/2007 | Kaczka | A61M 16/0096 137/458 |
| 2007/0144518 A1 * | 6/2007 | Acker | A61B 5/0836 128/204.21 |
| 2008/0000475 A1 * | 1/2008 | Hill | 128/204.18 |
| 2008/0029096 A1 * | 2/2008 | Kollmeyer | A61M 16/0051 128/204.21 |
| 2008/0087284 A1 * | 4/2008 | Krueger | A61M 16/0096 128/204.21 |
| 2008/0196720 A1 | 8/2008 | Kollmeyer et al. | |
| 2008/0245368 A1 | 10/2008 | Dunsmore et al. | |
| 2009/0126734 A1 * | 5/2009 | Dunsmore et al. | 128/203.25 |
| 2010/0252041 A1 | 10/2010 | Kapust et al. | |
| 2011/0100360 A1 | 5/2011 | Faram | |
| 2011/0146681 A1 * | 6/2011 | Jafari | A61B 5/085 128/204.21 |
| 2012/0304988 A1 * | 12/2012 | Meyer | A61M 16/208 128/204.21 |
| 2013/0008444 A1 * | 1/2013 | Chalvignac et al. | 128/204.21 |
| 2013/0133655 A1 * | 5/2013 | Kimm | A61M 16/205 128/204.23 |
| 2014/0150791 A1 * | 6/2014 | Birnkrant | A61M 16/0006 128/204.23 |
| 2014/0373844 A1 * | 12/2014 | Brand et al. | 128/204.22 |
| 2015/0238724 A1 * | 8/2015 | Lindstrom | A61M 16/0096 128/204.21 |

OTHER PUBLICATIONS

International Search Report and Written Opinion for International Application No. PCTUS2014031264, dated Aug. 11, 2014, 9 Pages.
Extended European Search report for EP14770097.5; dated Dec. 23, 2016.

* cited by examiner

PORTABLE VENTILATOR SECRETION MANAGEMENT SYSTEM

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present disclosure relates generally to patient ventilation systems, and more particularly to a secretion management system and method for a wearable or otherwise portable ventilator in which high frequency pressure/airflow oscillations are selectively generated to mobilize secretions within a patient's respiratory tract.

2. Related Art

The respiration system of the human body provides needed oxygen intake, oxygen/carbon dioxide exchange, and carbon dioxide expulsion functions, each of which involves the lungs. In this regard, the lungs function as a gas-exchanging organ in which inhaled oxygen is passed to the blood, and collected carbon dioxide is passed from the blood to the air. Additionally, the lungs function as a respiratory pump that transports oxygen-rich air into the lungs, and the carbon dioxide-rich air out of the lungs. The breathing center in the brain, central and peripheral nerves, the osseous thorax and the breathing musculature as well as free, stable respiratory paths are necessary for a correct functioning of the respiratory pump.

With patients suffering from certain diseases or other serious medical conditions, there is a constant overload on or exhaustion of the respiratory pump. A typical syndrome is pulmonary emphysema with flat-standing diaphragms without the ability to contract, and the respiratory paths are usually extremely slack and tend to collapse. Consequentially, the patient experiences difficulty with breathing deeply enough and providing the body with needed oxygen while also expelling waste carbon dioxide.

Mechanical ventilators comprise medical devices that either perform or supplement breathing for patients. Conventional ventilators use positive pressure to deliver gas to the patient's lungs via a patient circuit between the ventilator and the patient. The patient circuit typically consists of one or two large bore tubes (e.g., 22 mm inner diameter for adults; 15 mm inner diameter for pediatrics) that interface to the ventilator on one end and a patient mask on the other end. The ventilator applies positive pressure to open the patient's airway to prevent its collapse. In basic implementations, the rate and volume of inhalation and exhalation cycles is set by the ventilator without regard to the patient's spontaneous breathing cycle. However, there are also conventional devices that adjust delivery of ventilation gas based upon patient respiration.

As a part of normal body functioning, mucus is secreted to cover and protect the surface area of the respiratory pathways. It is understood that the clear secretions of mucus trap small debris, pollutants, and particulates as well as infectious disease agents passing through the oral/nasal cavities, pharynx, larynx, trachea, bronchi, and the lungs before it can invade the membranes thereof. In a healthy state, the mucus is expelled by the coordinated and continuous wave-like movement of the ciliated epithelia that line the bronchi and trachea. This movement, also referred to as the mucociliary escalator, pushes up the mucus as far as the junction between the trachea and the larynx, where it may be passed to the esophagus. Excesses that cannot be handled solely by the mucociliary escalator can be removed by coughing.

With the aforementioned weakening of the respiratory system, the ability to expel the mucus may be diminished. However, it is often the case that the infections that are the root causes of diminished respiratory function promote increased production of mucus. The combined effects of more mucus being produced and less of it being expelled through coughing and the action of the mucociliary elevator generally results in the increased retention of mucous within the respiratory tract. This is understood to promote the growth of pathogens, which further exacerbates the condition of the patient. Accordingly, it is expelling mucus from the airways that is critical, particularly for patients suffering from conditions that require breathing augmentation with ventilators, who already have weakened respiratory systems.

One conventional modality for facilitating the removal of mucus from the lungs may be categorized into a genus of like devices all characterized by a valve placed in-line with the patient circuit and is opened and closed rapidly as breathing gas is delivered to the patient. This is understood to induce turbulence or flutter resulting in pressure spikes that promote the movement of mucus. Instead of valves, other oscillating components such as pistons and electromagnetic transducers have also been substituted. Other modalities in which external stimulation of the upper thoracic area is provided in conjunction with the foregoing airway stimulation are also known.

However, these devices may be problematic in a number of different respects. More particularly, conventional devices tend to be ill suited for portable ventilation applications because of the cumbersomeness associated with external components that must be placed along the patient circuit. Furthermore, existing approaches do not have sufficient response characteristics to make high frequency oscillation of the extent necessary for affecting mucus expulsion without complicated vacuum pumps that generate needed reverse pressure for the negative parts of the oscillation. Accordingly, there is a need in the art for an improved wearable ventilator secretion management system.

BRIEF SUMMARY

In accordance with one embodiment of the present disclosure there is contemplated a portable patient ventilation apparatus. The apparatus may include an intake port connectible to a pressure source that provides a predefined source flow rate of therapeutic breathing gas. Additionally, there may be a patient circuit output port that is connectible to a patient interface for fitment on a patient respiratory passageway. There may be a valve with an input that is in pneumatic communication with the intake port and an output in pneumatic communication with the patient circuit output port. The valve may have variable open and closed positions that correspond to specific restriction factors against the predefined source flow rate of the therapeutic breathing gas from the pressure source. The apparatus may further include a flow sensor in pneumatic communication with the variable position valve and the patient circuit output port. There may also be a controller that is in communication with the flow sensor and the variable position valve. A patient inspiratory phase and a patient expiratory phase may be detectable by the controller from flow sensor measurements, in order to induce oscillations in delivery of the therapeutic breathing gas to the patient circuit output port. The oscillations may be based upon a periodic switching of the valve in sequence between the variable open and closed positions during at least a selected one of the patient expiratory and inspiratory phases.

According to another embodiment of the present disclosure, patient ventilator secretion management system is contemplated. The system may include a valve with an input in pneumatic communication with a therapeutic breathing gas source. The valve may have variable positions, each of which corresponds to a specific flow rate of gas being output from the valve. The system may further include a patient ventilation interface in pneumatic communication with the valve over a gas delivery circuit. There may also be a controller in communication with the valve for regulating the position thereof. The controller may sequentially switch the valve from one of the variable positions to another one of the variable positions to output a first range of fluctuating flow rates of gas for delivery to the patient ventilation interface during at least a selected one of patient expiratory and inspiratory phases.

Yet another embodiment of the present disclosure is directed to a method for managing mucus secretion of a patient undergoing ventilation therapy with a ventilation apparatus. The method may include receiving a therapeutic breathing gas delivery volume for the patient. This may be received on a controller data processing apparatus of the ventilation apparatus. There may also be a step of receiving at least one oscillation frequency value and at least one oscillation magnitude value. Again, this may be received on the controller data processing apparatus. The method may continue with generating a first valve positioning signal on the controller data processing apparatus. The first valve positioning signal may have a value corresponding to the oscillating magnitude value. Thereafter, the method may include applying the first valve positioning signal to a valve for positioning a valve element to deliver a first predetermined flow rate of therapeutic breathing gas to the patient at a first time instance. There may additionally be a step of generating a second valve positioning signal that may have a value corresponding to the oscillating magnitude value but different from the first valve positioning signal. The method may further include applying the second valve position signal to the valve for positioning the valve element to deliver a second predetermined flow rate of the therapeutic breathing gas to the patient at a second time instance different from the first time instance. The oscillation frequency value may correspond to a difference between the first time instance and the second time instance.

Certain other embodiments of the present disclosure contemplate respective computer-readable program storage media that each tangibly embodies one or more programs of instructions executable by a data processing device to perform the foregoing method. The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

The detailed description set forth below in connection with the appended drawings is intended as a description of the several presently contemplated embodiments of a secretion management system for a patient ventilation apparatus. The system delivers breathing gas to a patient for respiratory assistance and implements various methods for generating high frequency oscillation at selected segments of the patient breathing cycle at certain defined levels. This description is not intended to represent the only form in which the disclosed invention may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figure 1:
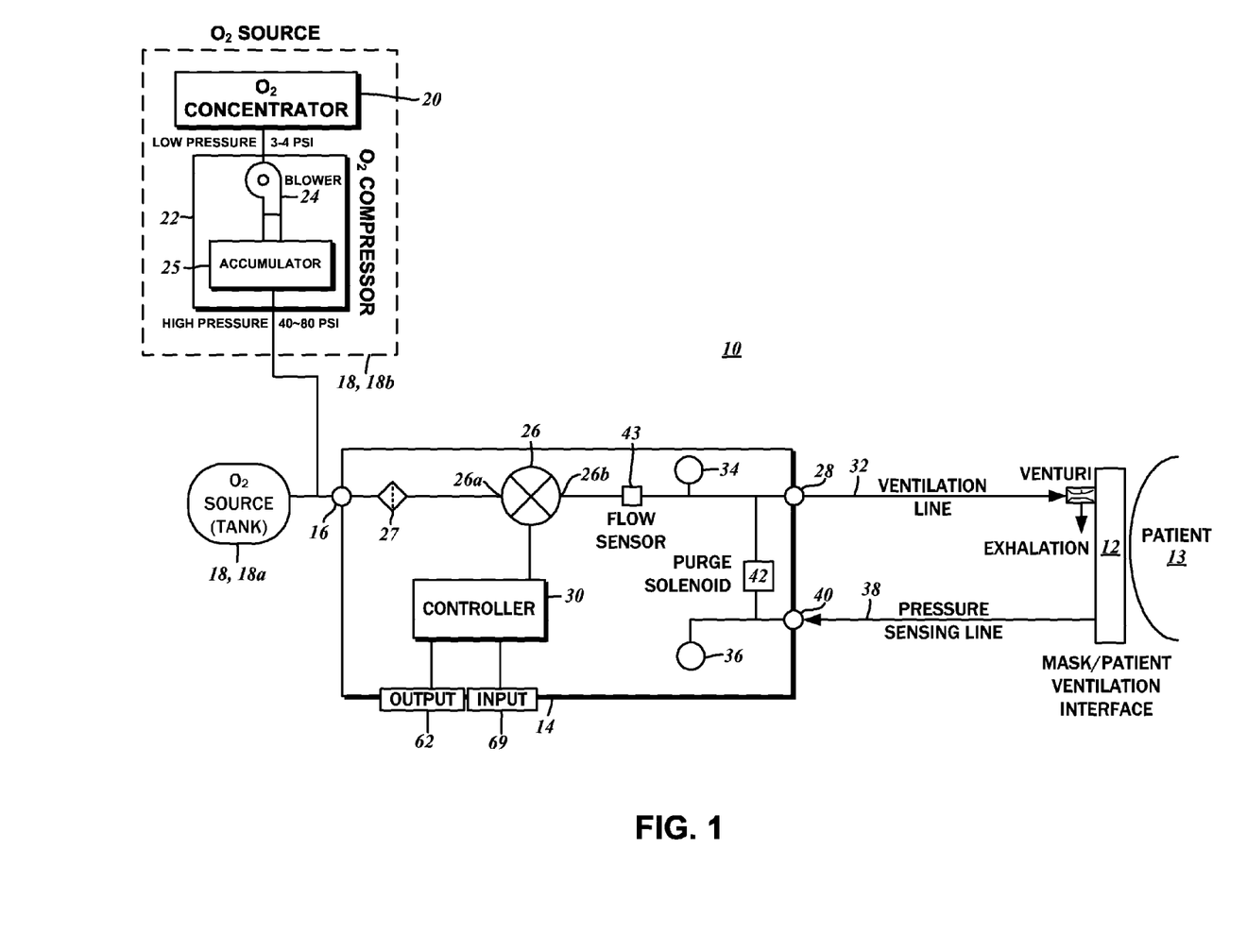
FIG. 1 is a block diagram showing the components of a ventilator apparatus in accordance with various embodiments of the present disclosure including a ventilation unit, a patient ventilation interface, gas passage conduits, and oxygen sources.

Referring to the block diagram of FIG. 1, one embodiment of a ventilation system 10 is generally comprised of a patient ventilation interface 12 and a ventilation unit 14. The patient ventilation interface 12 may include such devices as a full-face mask or a nasal mask that can be placed in direct gas flow or pneumatic communication with the upper respiratory tract of a patient 13, i.e., the nasal cavity and/or the oral cavity. It will be appreciated that other apparatuses that so interface the respiratory system of the patient to the ventilation unit 14, either non-invasively or invasively, may be substituted without departing from the scope of the present disclosure, so long as certain features noted below are incorporated therein.

Generally, the ventilation unit 14 generates a flow of breathing gas that is delivered to the patient via the patient ventilation interface 12. The breathing gas may be a combination of ambient air enriched with oxygen, or any other suitable mixture of gas appropriate for treating the patient. The ventilation unit 14 includes a first inlet port 16, through which oxygen enriched gas may be provided by an oxygen source 18. A first type of oxygen source is a tank 18a, which stores compressed, oxygen enriched gas. Alternatively, there may be a second type, which is comprised of an oxygen concentrator device 20 that intakes ambient air and outputs a lower pressure oxygen-enriched gas to an oxygen compressor 22. According to one embodiment, the oxygen concentrator 22 generates an output pressure of approximately 3 to 4 psi. In further detail, the oxygen compressor 22 includes a blower device 24 that increases the pressure of gas flow ported from the oxygen concentrator 20 for storage in an accumulator 25. Output from the accumulator 25 is regulated at a comparatively higher pressure of approximately 40 to 80 psi. The first inlet port 16 of the ventilation unit 14 is in communication with an inlet filter 27 that removes particulates and other contaminants from the breathing gas that is ultimately delivered to the patient.

The high pressure originating from either of the oxygen sources 18a, 18b is regulated by a valve 26. There is a valve inlet port 26a in gas flow communication with the inlet filter 27, and a valve outlet port 26b that is in gas flow communication with an outlet port 28 of the ventilation unit 14. As will be described in further detail below, the position of the valve 26 is selectively adjusted to port a desired volume/pressure of gas from the oxygen sources 18 to the patient 13. It will be recognized that any suitable valve 26 capable of regulating gas flow and pressure for ventilating a patient in accordance with the present disclosure may be utilized. The valve 26 may be driven electrically, pneumatically, or any other suitable motive modalities. The actuation of the valve 26 is governed by a programmable controller 30 that implements the various methods of patient ventilation and secretion management/mobilization contemplated by the present disclosure, as will be described in further detail below.

The flow of breathing gas that is ported through the valve 26 is passed through the outlet port 28 to a gas delivery conduit 32 that is coupled to the aforementioned mask or patient ventilation interface 12. The gas delivery conduit 32 is understood to be a plastic tube having a predetermined inner diameter such as 22 mm or smaller, though any other conduit of suitable material and construction may be utilized. A pressure difference is generated between the patient ventilation interface 12 and the output of the valve 26, i.e., the valve outlet 26a depending on the state of respiration of the patient 13.

In order to ascertain such pressure differentials, the presently contemplated ventilation system 10 includes dual pressure sensors, including a valve pressure sensor 34 and a patient interface pressure sensor 36. The valve pressure sensor 34 is disposed within the ventilation unit 14, and monitors the pressure at the valve outlet port 26b. The patient interface pressure sensor 36 is also physically disposed within the ventilation unit 14, but is in direct gas flow communication with the patient ventilation interface 12 over a pressure sensing line 38 that is connected to a sensor inlet port 40 of the ventilation unit 14. When the ventilation unit 14 is operating, gas pressure within the pressure sensing line 38 as well as the gas conduit 32 may be connected to deliver a purge flow to clear the pressure sensor line 38. This can be done through a purge solenoid 42 connected to both. The purge can be continuous or intermittent according to the patient's breathing phase or pressure difference between the valve pressure and the patient interface pressure.

With the reduced diameter of the gas delivery conduit 32, particularly in relation to a larger diameter sections of the gas flow passageway through the valve 26, there are increased flow rates at lower pressures at the patient ventilation interface 12. As will be recognized by those having ordinary skill in the art, a Venturi effect is exhibited. Additional ambient air may be entrained as a result, providing greater therapeutic breathing gas flow to the patient 13.

In addition to measuring pressure differentials at the patient ventilation interface 12 and the valve output 26b, flow measurements of the breathing gas actually output from the valve 26 are utilized. To this end, the ventilation unit 14 includes a flow sensor 43 that is in-line with the valve 26 and the outlet port 28.

Figure 2:
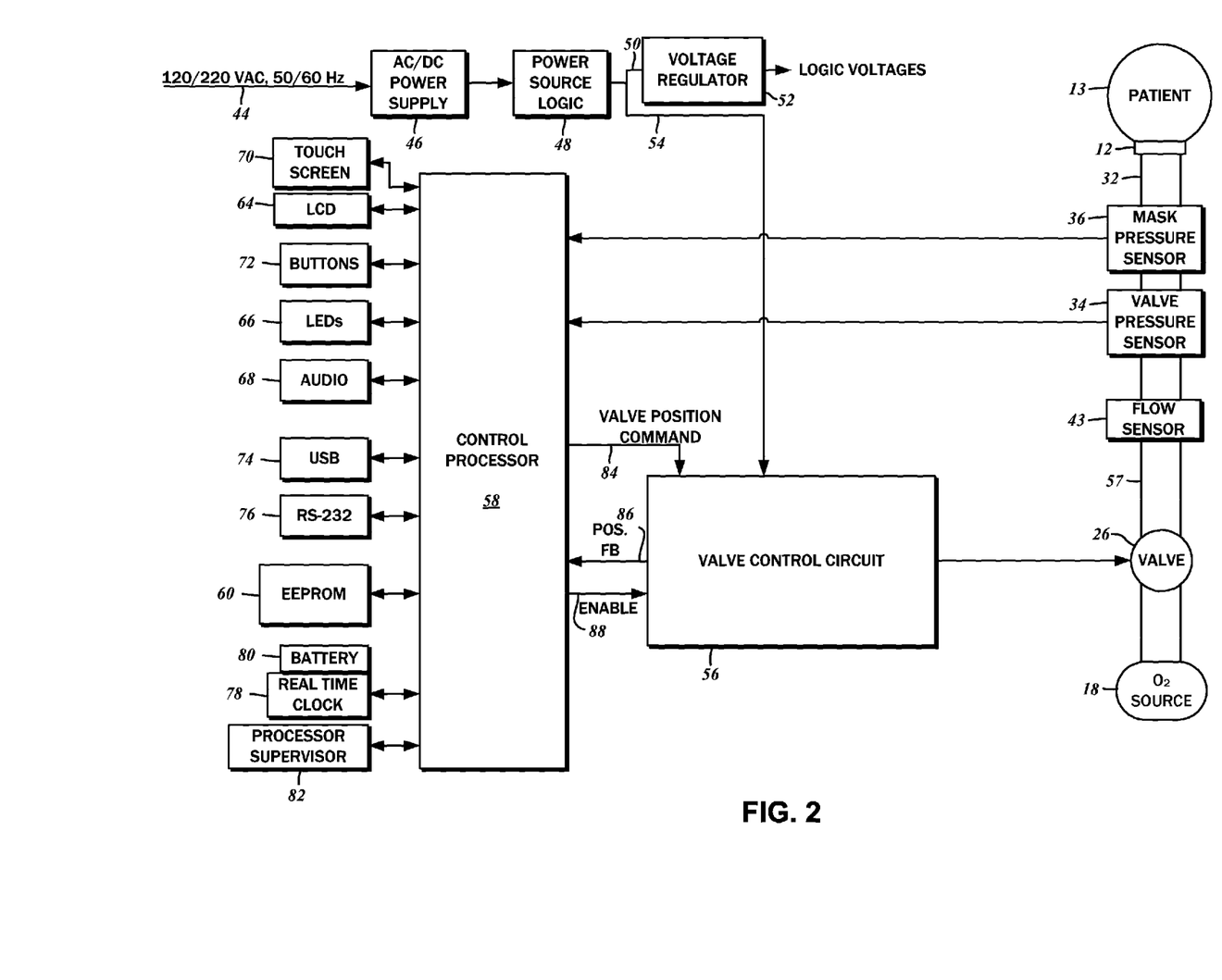
FIG. 2 is a block diagram illustrating the electrical components of the ventilation unit.

The block diagram of FIG. 2 illustrates the various electrical components of one typical embodiment of the ventilation unit 14. Power for the ventilation unit 14 may be provided from a conventional household electricity supply of either 120V or 220V alternating current (AC), at 50 Hz or 60 Hz. The block diagram denotes this supply as a power source 44. A power supply 46 is connected to the power source 44, and as will be recognized by those having ordinary skill in the art, the power signal is variously rectified, filtered, and stepped down to a direct current (DC) voltage. In accordance with one embodiment of the present disclosure, the DC voltage source is 24 V. Some components of the ventilation unit 14 may utilize higher DC voltages than control logic devices, and so the power supply 46 is connected to a power source logic 48. A first output 50 of the power source logic 48 is connected to an integrated circuit voltage regulator 52 that steps down the DC voltage to the logic device level of 5V. A second output 54 of the power source logic 48 is the existing high DC voltage directly from the power supply 46, and is connected to a valve control circuit 56.

The continuous source of oxygen enriched breathing gas is provided by the oxygen source 18 as discussed above, and the output to the patient ventilation interface 12 and eventually to the patient 13 is regulated by the valve 26. The specific position of the valve 26 needed for the determined volume and pressure of breathing gas is set by the valve control circuit 56, and those having ordinary skill in the art will recognize implementations of valve actuators that are suitable for the contemplated application. From the opening of the valve 26, breathing gas flows through an internal conduit 57 that is in-line with the flow sensor 43. The internal conduit 57 is coupled to the aforementioned outlet port 28 of the ventilation unit 14, which in turn is coupled to the gas conduit 32. As described above, the valve pressure sensor 34 and the patient interface pressure sensor 36 are connected to the pneumatic circuit between the valve 26 and the patient 13.

The programmable controller 30 and its functionality may be implemented with a programmable integrated circuit device such as a microcontroller or control processor 58. Broadly, the control processor 58 receives certain inputs, and based upon those inputs, generates certain outputs. The specific operations that are performed on the inputs may be programmed as instructions that are executed by the control processor 58. In this regard, the control processor 58 may include an arithmetic/logic unit (ALU), various registers, and input/output ports. Although external memory such as EEPROM (electrically erasable/programmable read only memory) 60 may be connected to the control processor 58 for permanent storage and retrieval of program instructions, there may also be an internal random access memory (RAM). One embodiment contemplates the use of an Intel® 8081 instruction set/architecture, though any other suitable instruction set or processor architecture may be substituted. As indicated above, the control processor 58 is powered by a low voltage DC supply from the voltage regulator 52.

In order to set the operational parameters of the ventilation unit 14, and to initiate or terminate certain functions, a graphical user interface is provided. Such graphical user interface may generated on an output device 62, which may be of a liquid crystal display (LCD) type 64. Any graphic may be shown on the output device, though for more specific indicators, a simple light emitting diode (LED) device 66 may be utilized. It will be recognized that alarm conditions, power status, and the like may be indicated with the LED device 66. Audible outputs may also be produced with audio transducers 68 that are likewise connected to the control processor 58. Among the contemplated outputs that may be generated on the audio transducer 68 include simple beeps and alarms, as well as sophisticated voice prompts that provide information and instructions.

An operator may interact with the graphical user interface through different input devices 69 such as a touch screen interface 70 that is overlaid on the LCD screen 64. It will be recognized that various graphic elements may be generated on the underlying screen 64, with touch inputs/interactions corresponding in position to those graphic elements being evaluated as a selection or activation of the same. Various touch screen interfaces, some of which may be directly integrated with the screen 64, are known in the art. Besides touch screen inputs, buttons 72 may also be connected to the control processor 58 for similarly receiving user inputs. It is understood that the audio transducer 68 may also accept sound input in the form of voice commands, the processing of which is performed may be performed by the control processor 58.

Several modalities for connecting to and communicating with other data processing devices such as general-purpose computers are also contemplated. Accordingly, the control processor 58 may be connected to a universal serial bus (USB) controller 74. For more basic communications, there may be a serial RS-232 transceiver 76. Through these data communications modalities, the configuration options of the ventilation unit 14 may be set, operating profiles may be downloaded, and so forth. Notwithstanding the specific reference to USB and RS-232 communications modalities, any other communications modality including wireless systems may be substituted without departing from the present disclosure.

The functions of the ventilation unit 14 depend on proper synchronization, and so the control processor 58 is connected to a real time clock 78 that maintains a common clock cycle. Although a primary feature of the real time clock 78 is to maintain synchrony at a processor cycle level, longer term time data is also maintained. In order to retain such time data, the real time clock 78 may be powered independently of the primary power source 46, and there is accordingly a battery backup 80. Under heavy processing loads or unexpected program conditions, the control processor 58 may become unable to execute critical programmed steps in real-time. Thus, the control processor 58 may include a processor supervisor 82 that invokes a program execution break upon detecting such conditions. Typically, this is implemented as a step of clearing a memory variable periodically, and when that step is unable to take place because instruction execution is frozen or otherwise delayed, the processor supervisor 82 may cause a predetermined routine to be executed.

As mentioned above, the valve 26 is driven by the valve control circuit 56, which generates different outputs depending on signals received from the control processor 58. The signal to drive the valve 26 is generated on a valve position command line 84. To confirm that the position of the valve 26 is actually where it has been commanded to be, the valve control circuit 56 provides feedback via a valve position feedback line 86. Furthermore, as detailed below, pressure readings at the patient 13 is utilized to reach control decisions, so the patient interface pressure sensor 36 is connected to the control processor 70. The valve control circuit 56 is activated and deactivated via an enable line 88.

As referenced herein, the terms patient ventilation interface 12 and patient mask are utilized interchangeably. It will be recognized that the patient mask is a specific kind of patient ventilation interface, and as explained briefly above, other types of ventilation interfaces may be utilized. Along these lines, reference to such terms as mask pressure, valve pressure, or the use of the term mask or valve to modify any other term is for purposes of convenience only and not of limitation. For instance, mask pressure is understood to refer to the pressure in the patient ventilation interface 12, while valve pressure refers to the pressure at the output of the valve 26.

In accordance with various embodiments of the present disclosure, the valve 26 is controlled by the programmable controller 30 to output therapeutic breathing gas in accordance with the inspiratory and expiratory phases of the patient 13. The determination of when each begins and ends is understood to be based upon pressure differences between the patient ventilation interface 12 and the valve outlet port 26*b* as detected by the patient interface pressure sensor 36 and the valve pressure sensor 34, respectively. How this is achieved is more fully set forth in co-pending U.S. patent application Ser. No. 13/841,189 filed Mar. 15, 2013 and entitled "PATIENT AND DEVICE PRESSURE DIFFERENTIAL BASED NON-INVASIVE VENTILATION," the disclosure of which is wholly incorporated by reference in its entirety herein.

Figure 3:
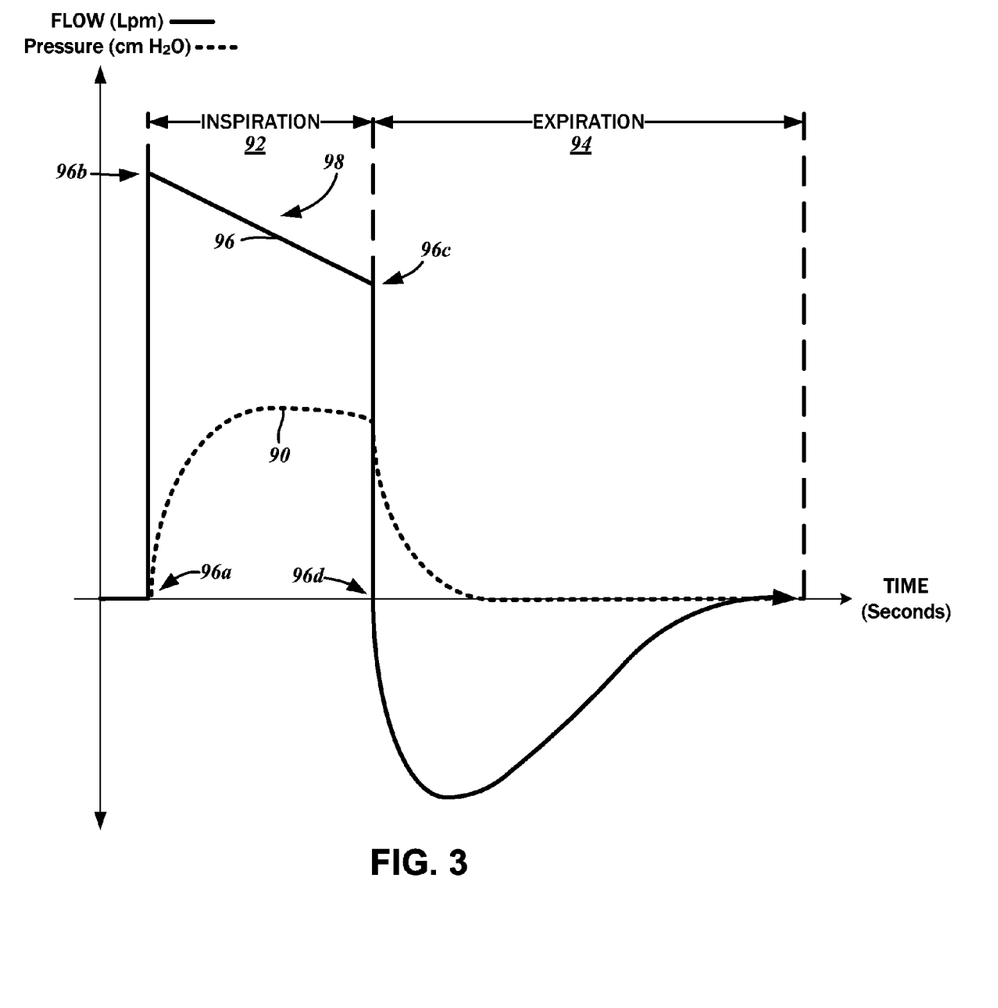
FIG. 3 is a graph illustrating a conventional flow rate of gas delivery to the patient and an example resultant mask pressure.

The graph of FIG. 3 illustrates pressure and flow rates as therapeutic breathing gas is provided to the patient ventilation interface 12 over a single respiration cycle. There is a first plot 90 corresponding to the pressure at the patient ventilation interface 12, including a positive pressure region (relative to the ventilation system 10) characterized by patient inspiration 92, and a negative pressure region characterized by patient expiration 94. Furthermore, a second plot 96 corresponds to the augmentation flow rate, that is, the flow rate as measured by the flow sensor 43 as the valve 26 is adjusted to deliver varying volumes of therapeutic breathing gas. As shown, the flow rate begins at a zero level at point 96*a*, which corresponds to the beginning of the patient inspiration 92. The flow rate then initially peaks at point 96*b* and decreases linearly along region 98 until reaching patient expiration 94 at point 96c, at which time augmentation flow decreases to zero at point 96d.

Figure 4A:
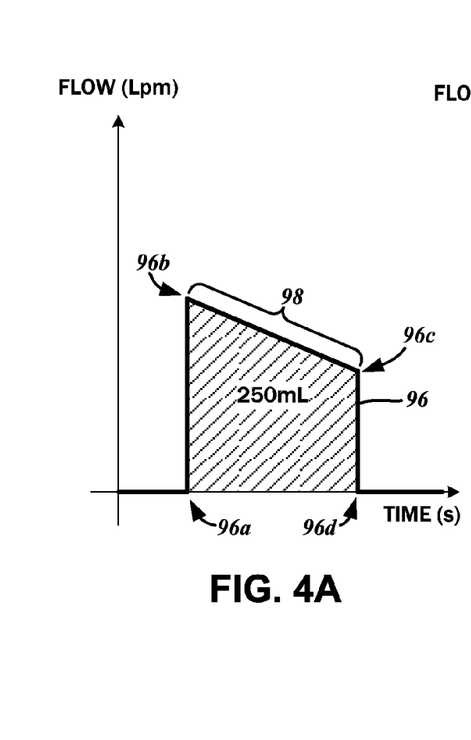
FIG. 4A is a graph charting a flow rate of therapeutic breathing gas being output at a valve for delivery to a patient over time in accordance with various embodiments of the present disclosure.

It is understood that with a constant flow rate of therapeutic breathing gas input to the ventilation unit 14 via the first inlet port 16, the positioning of the valve 26 regulates varying flow rates to the patient ventilation interface 12. The graph of FIG. 4A again illustrates the aforementioned flow control sequence responding to the patient inspiration 92, with the plot 96 and its defining points 96a-96d. Integration of the flow rate, given in liters per minute, yields the total volume of therapeutic breathing gas supplied to the patient 13. Typically, ventilation therapy is prescribed in terms of tidal volume (in mL) per inspiration, and in the example shown, is 250 mL. As will be described in further detail below, various embodiments of the present disclosure contemplate oscillations that alternately drive the flow rate lower and higher than the linear reduction shown. However, one objective is maintaining an average linear flow rate reduction that is consistent with the prescribed tidal volume per inspiration.

Figures 4B, 4C:
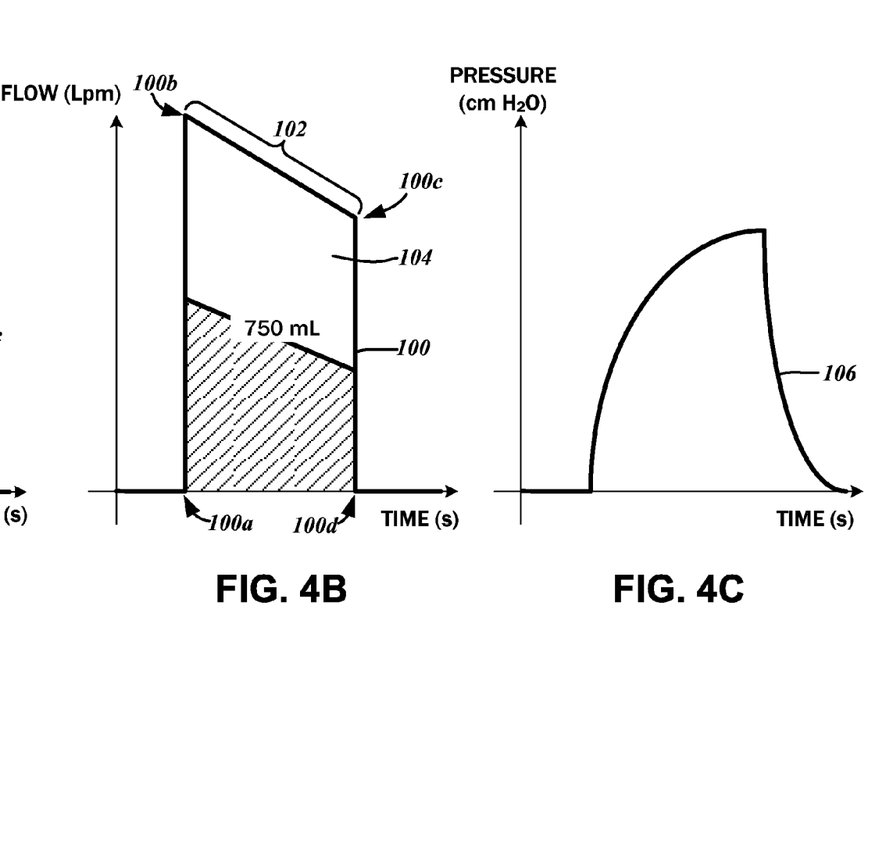
FIG. 4B is another graph charting a flow rate of therapeutic breathing gas being delivered to the patient over time with an increase volume and flow accounting for air entrainment resulting from Venturi effects.
FIG. 4C is a graph charting mask pressure at the patient over the same time period and airflow as shown in FIG. 4B.

As indicated above, one embodiment of the present disclosure contemplates the use of a patient ventilation interface 12 that entrains ambient air by way of a Venturi effect. The graph of FIG. 4B, and a third plot 100 thereof, is understood to represent the actual flow rate and volume at the patient ventilation interface 12. Similar to the plot 96 previously discussed, the flow rate initially is initially zero at point 100a, which corresponds to the beginning of the patient inspiration 92. The flow rate peaks at point 100b, and then decreases along region 102 until patient expiration 94 at point 100c. Flow then decreases to zero at point 100d. The additional area 104 is understood to correspond to the additional volume as a result of the entrainment. By way of example, in contrast to the 250 mL of therapeutic breathing gas produced at the valve outlet 26b, the actual volume provided to the patient 13 may be 750 mL. The corresponding pressure response at the patient ventilation interface 12 is shown in FIG. 4C as plot 106.

Figure 5A:
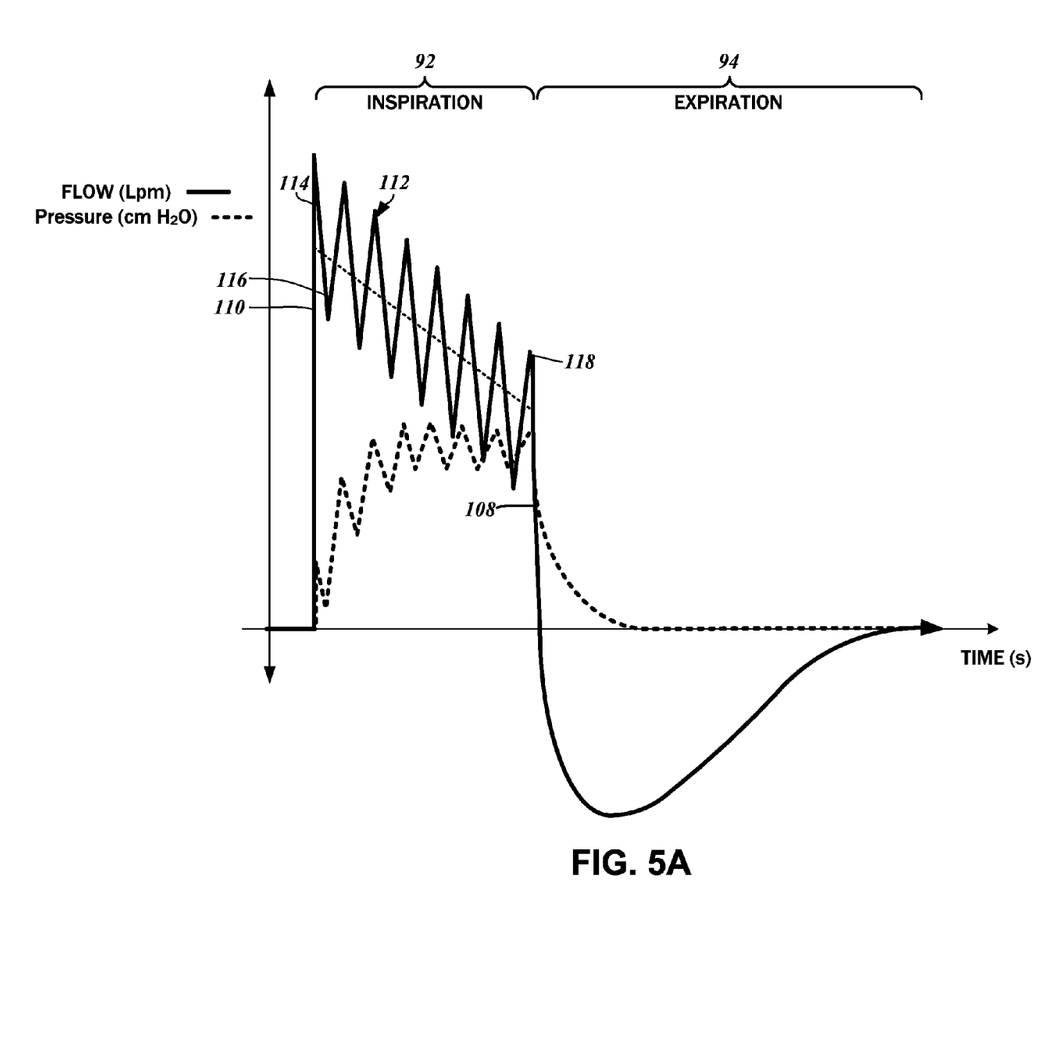
FIG. 5A is a graph illustrating a flow rate of gas delivery to the patient during inspiration in accordance with various embodiments of the present disclosure and the example resultant mask pressure.

FIG. 5A illustrates an example high frequency oscillation that is produced in the flow of therapeutic breathing gas that is delivered to the patient 13. The first plot 108 depicts the pressures at the patient ventilation interface 12 throughout respiration, while a second plot 110 corresponds to the augmentation flow rate. As contemplated herein, the oscillation 112 is understood to occur as a result of controlling the valve 26 to pass therapeutic breathing gas at a faster or slower flow rate for delivery to the patient ventilation interface 12 at various instances in time relative to a set value that is based upon the prescribed tidal volume. With concurrent reference to the graph of FIG. 3, the oscillation 112 corresponds in time with the decreasing region 102 of the first plot 90.

The difference in magnitude between a given peak 114 and its subsequent valley 116 is understood to be user-defined, as is the frequency of the oscillation, or the time between a given peak 114 and its immediate subsequent valley 116. Because the flow rate is at its relative peak and at its relative valley for equal durations over the inspiration cycle, the average flow rate is understood to be that of the set value. Thus, the total delivered volume is also understood to be the same as without oscillation. This is depicted in a third plot 118 that corresponds to the flow rate of delivering the therapeutic breathing gas to the patient 13 without oscillation, as shown in the second plot 96 of FIG. 3, above.

Although the oscillation 112 is shown as a triangular waveform, the valve 26 can be operated to achieve any other suitable periodic response.

According to one embodiment, the magnitude may be specified in relative terms that are easily understandable to the patient 13, such as low, medium, and high, which are subsequently translated into constant values that are used to control the valve 26. Alternatively, it may be specified in actual numerical values that represent the liters-per-minute differences to the set value of the flow rate, and also provided to the programmable controller 30 to vary the positioning of the valve 26. The oscillation frequency may also be set by the user in terms of an indeterminate value along a continuum of values ranging from a minimum to a maximum rather than a specific numeric frequency. Those having ordinary skill in the art will recognize that there are numerous ways in which settings such as oscillation magnitude and frequency may be set depending on the specifics of the user interface. Any suitable interface modality may be substituted without departing from the scope of the present disclosure.

Figure 5B:
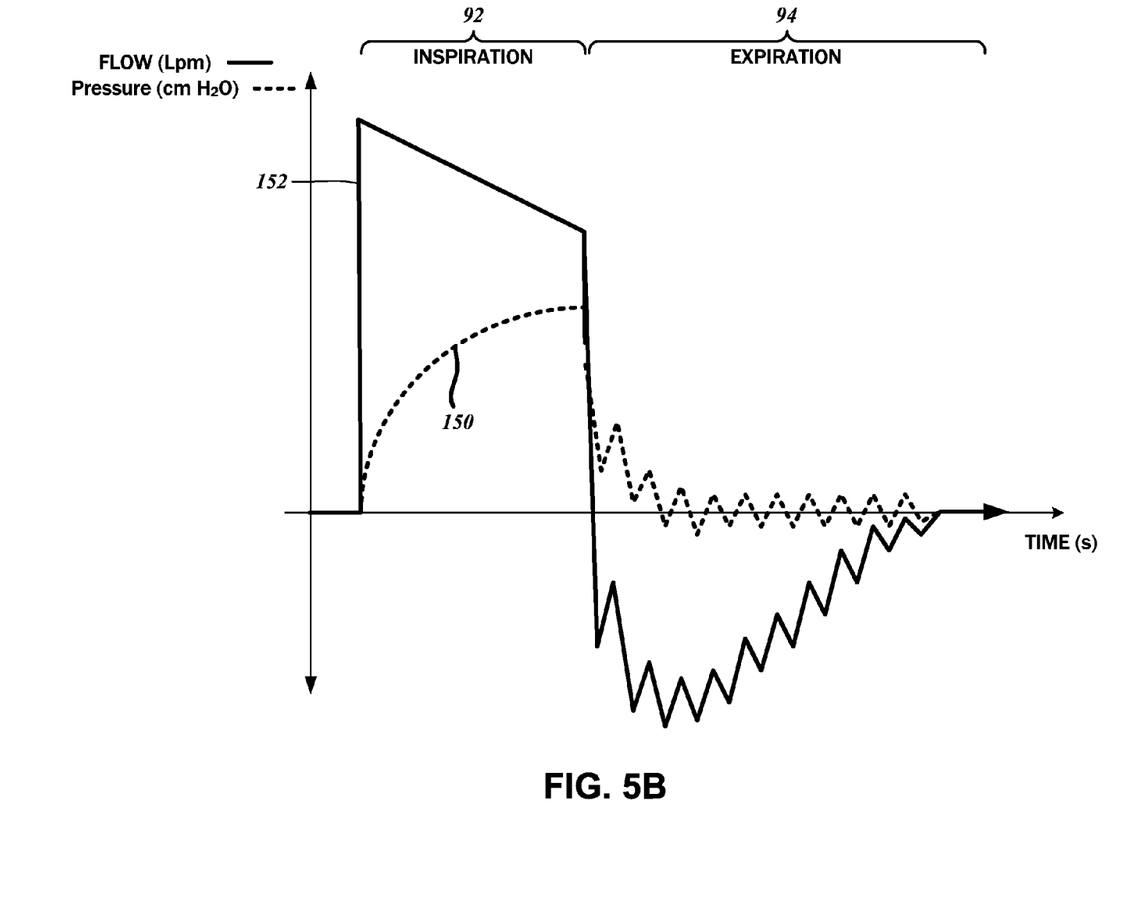
FIG. 5B is a graph illustrating a flow rate of gas delivery to the patient during expiration and the example resultant mask pressure.

The air flow oscillations are understood to mobilize the mucus or secretions within the respiratory passageway. In the illustrated example, the oscillation is generated during delivery of inspiratory gas to the patient 13 based upon the variable positioning of the valve 26. However, it is also possible for the oscillation to be generated during patient expiration. The graph of FIG. 5B illustrates this functionality. A first plot 150, similar to the first plot 108 discussed above in relation to FIG. 5A, depicts the pressures at the patient ventilation interface 12 throughout respiration, though with the oscillation being generated only during expiration. A second plot 152 corresponds to the augmentation flow rate. Thus, it is possible to generate oscillation in flow rates across the entirety of the patient breathing cycle, though it is selectively for each inspiratory and expiratory phases. Furthermore, it is possible to generate the oscillation during only a portion of the inspiratory and/or expiratory phases.

It is expressly contemplated that due to the sufficient pressures and corresponding flow rates at the patient ventilation interface 12, transport delays between the valve output 26b and the patient 13 are minimized, and the lower flow rates corresponding to the valleys 116 can be induced without vacuums mechanisms or other pumps that provide reverse pressure. The alternating valve positions are understood to be adequate for achieving this response.

Figure 6A:
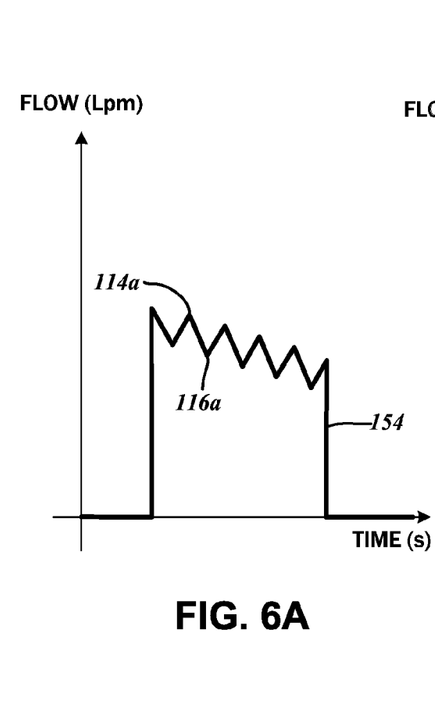
FIG. 6A is a graph charting an oscillating flow rate of therapeutic breathing gas being output at the valve.
Figure 6B:
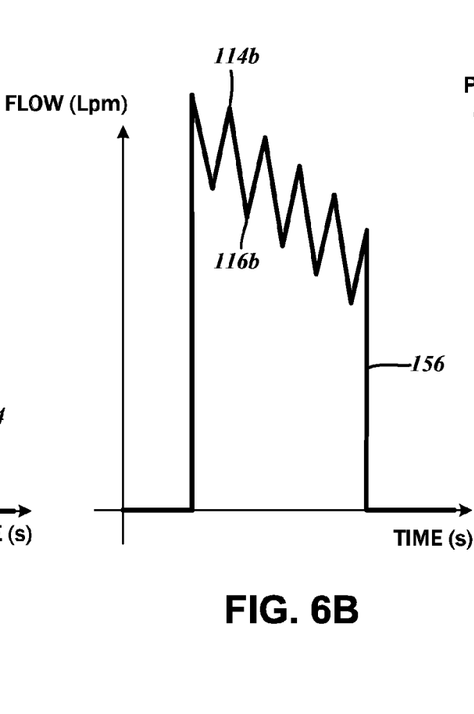
FIG. 6B is a graph charting a flow rate of therapeutic breathing gas being delivered to the patient with increased volume, flow, and oscillation magnitude attributable to Venturi effects.
Figure 6C:
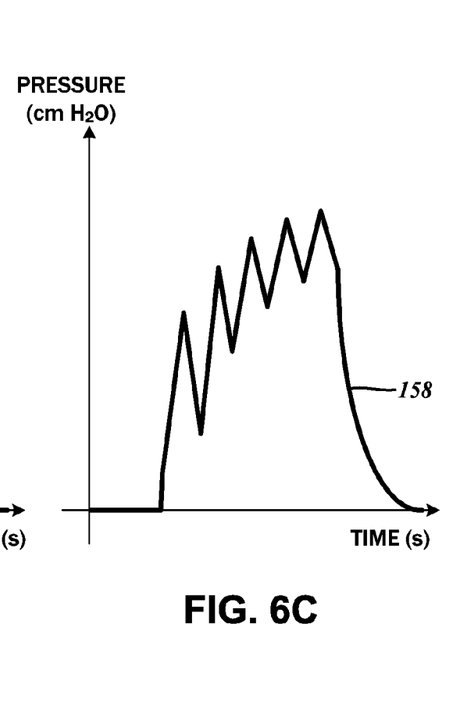
FIG. 6C is a graph charting oscillating mask pressure at the patient over the same time period and airflow as shown in FIG. 6B.

With reference to the graph of FIG. 6A, a plot 154 illustrates the oscillating flow of therapeutic breathing gas as it is output from the valve 26. In comparison, FIG. 6B and a plot 156 thereof illustrates the oscillating flow of therapeutic breathing gas as delivered to the patient 13, along the same flow rate and time scales. Furthermore, FIG. 6C and plot 158 depicts the same oscillations in pressure at the patient ventilation interface 12. As indicated above, with the differential flow rates and pressure resulting from the Venturi effects in the interface between the gas delivery conduit 32 and the patient ventilation interface 12, additional flow/volume of ambient air is entrained. FIGS. 6A and 6B illustrate the relative difference in flow rates resulting therefrom. It is also understood that the relative magnitude of the oscillations are increased, as depicted in a first peak 114a and a first valley 116a of the plot 154, compared to a corresponding second peak 114b and a second valley 116b of the plot 156.

At least in part because of this characteristic, relatively lower flow rates and flow rate differences/oscillation magnitudes can be induced at the valve output 26b, while achieving relatively higher flow rates and flow rate differences/oscillation magnitudes at the patient ventilation interface 12. Again, due to the pressure characteristics of utilizing a narrower diameter gas delivery conduit, which in one embodiment is less than 8 mm, flow rate changes can be effectuated at higher speeds. In this regard, the frequency of oscillation exhibited at the valve output 26b is the same as at the patient ventilation interface 12. Furthermore, with the exhalation valve of the patient ventilation interface 12 being closer to the patient 13, negative pressures can be induced quickly. Without the need for the aforementioned pistons and other components that may otherwise be needed to achieve the foregoing performance characteristics, it is possible for the ventilation unit 14 to occupy a smaller footprint. Indeed, it is expressly contemplated that the ventilation system 10 is portable and wearable by the patient 13.

Figure 7:
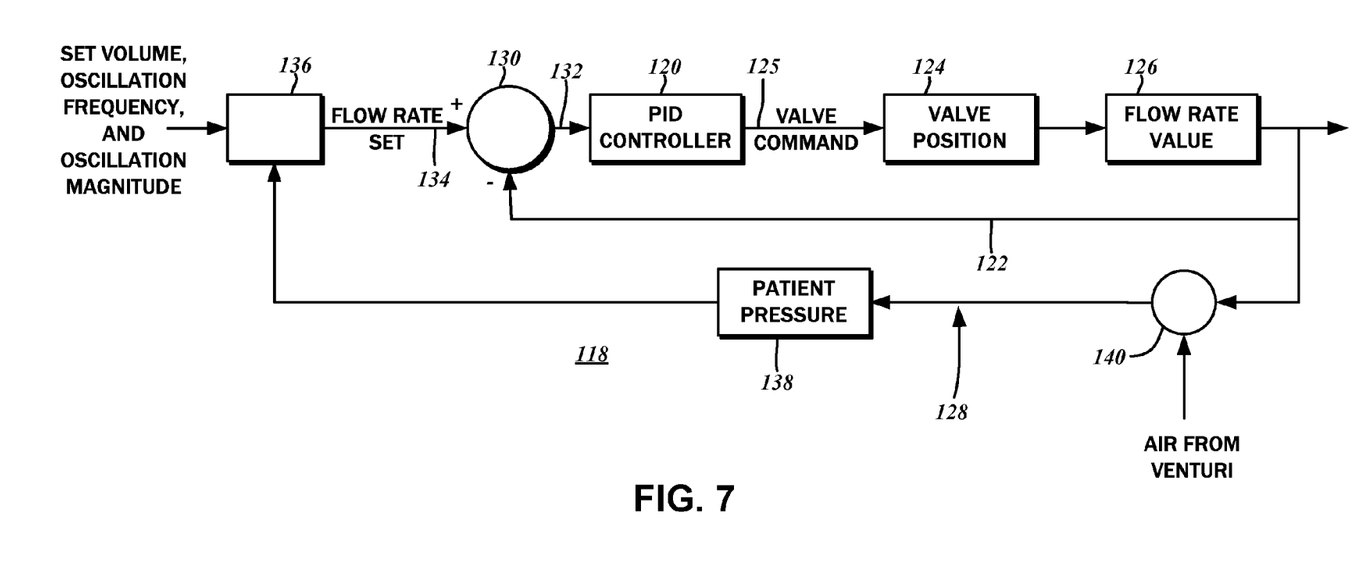
FIG. 7 is a control loop block diagram depicting a patient ventilation interface high frequency flow oscillation control.

Referring now to the control loop block diagram of FIG. 7, additional details pertaining to the control functions of the valve 26, and specifically a closed/open loop control circuit 118 to manipulate the valve 26 to achieve the above-described function of the therapeutic breathing gas delivery with high frequency oscillation, will be described. The control circuit 118 includes a PID controller 120 that acts upon the valve 26 to effectuate pressure and flow rate changes within the patient circuit. There is a control loop 122 in which the first PID controller 120 regulates a valve position 124 with a valve command output 125. This, in turn, regulates flow as measured by the flow sensor 43, depicted as a flow rate value 126. A summing point 130 generates an output signal 132 to the PID controller 120 that drives the valve 26, with the output signal 132 resulting from a flow rate set point 134 and the actual flow rate value 126 measured by the flow sensor 43. The flow rate set point 134 is further based upon a set ventilation volume, oscillation frequency, and oscillation magnitude as specified to a therapy values input block 136.

The control loop 122 in its most basic form is understood to be open, as there is no feedback from the output variable, i.e., pressure at the patient 13. However, with the addition of a patient pressure 138 measured by the patient interface pressure sensor 36, the control loop 126 is understood to be closed. A secondary control loop segment 128 utilizes the flow value 126 provided to a second summing point 140, and factors in the additional airflow attributable to the aforementioned air entrainment resulting from Venturi effects. This affects the flow rate set point 134, as it is provided to the therapy values input block 136.

Figure 8:
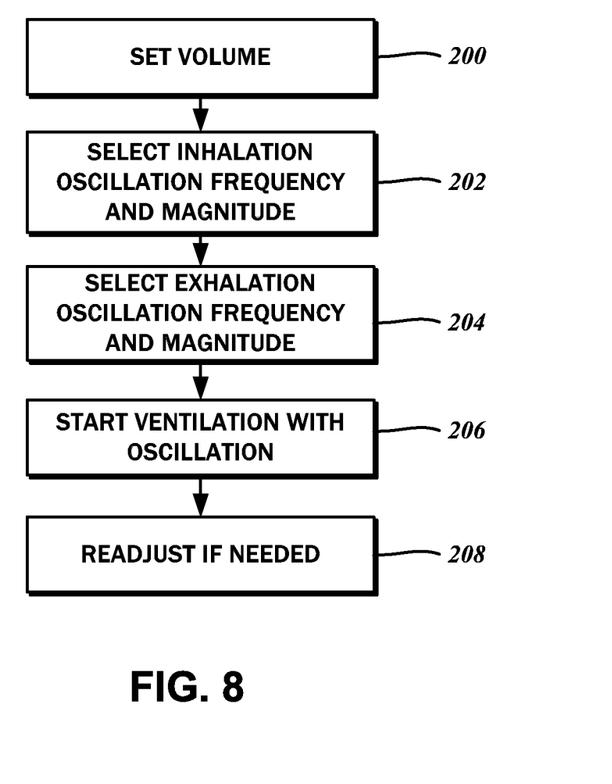
FIG. 8 is a flow chart depicting one operational method of a ventilator apparatus.

In accordance with various embodiments of the present disclosure, a method for operating the ventilation system 10 is also contemplated. With reference to the flowchart of FIG. 8, per step 200, the volume of therapeutic breathing gas that is delivered to the patient 13 is set. Thereafter, per step 202, the desired oscillation frequency and magnitude for the inspiratory flow is set according to the various modalities discussed above. Optionally, in a step 204, the desired oscillation frequency and magnitude for the expiratory flow is set. Ventilation therapy then commences in a step 206, with the parameters (oscillation frequency and magnitude) may be re-adjusted based upon different user inputs per step 208.

The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show details of the present disclosure with more particularity than is necessary, the description taken with the drawings making apparent to those skilled in the art how the several forms of the present disclosure may be embodied in practice.

What is claimed is:

1. A portable patient ventilation apparatus comprising:
an intake port connectable to a pressure source providing a predefined source flow rate of therapeutic breathing gas;
a ventilator output port connectible over a gas delivery circuit to a patient ventilation interface for fitment on a patient respiratory passageway;
a valve with an input in pneumatic communication with the intake port and an output in pneumatic communication with the ventilator output port, having variable open and closed positions;
a first pressure sensor measuring a patient ventilation interface pressure, the patient ventilation interface being connectible to the first pressure sensor over a pressure sensor line;
a second pressure sensor measuring a valve output pressure; and
a controller in communication with the first pressure sensor, the second pressure sensor, and the valve, a patient inspiratory phase and a patient expiratory phase being detectable by the controller based upon a combination of measurements of the first pressure sensor and the second pressure sensor, the controller being operative to switch the valve to restrict the flow of therapeutic breathing gas through the valve, the controller being further operative to periodically switch the valve in sequence between the variable open and closed positions during at least a selected one of the patient expiratory and inspiratory phases to induce oscillations in the flow of therapeutic breathing gas through the patient ventilation interface within a selected patient expiratory or inspiratory phase with an oscillation magnitude of the oscillations being controlled based on the measurement of the first pressure sensor.

2. The apparatus of claim 1, wherein a rate of the periodic switching is defined by an oscillation frequency set by a user.

3. The apparatus of claim 1, wherein one oscillation cycle is defined by a first restricted flow rate corresponding to a first open position of the valve, and a second restricted flow rate corresponding to a first closed position of the valve.

4. The apparatus of claim 3, wherein the first restricted flow rate is defined as a first restriction factor applied against the predefined source flow rate, and the second restricted flow rate is defined as a second restriction factor applied against the predefined source flow rate.

5. The apparatus of claim 3, wherein a difference between the first restricted flow rate and the second restricted flow rate defines the oscillation magnitude.

6. The apparatus of claim 3, wherein:
the patient ventilation interface includes an entrainment port; and
the first restricted flow rate and the second restricted flow rate are at the output of the valve, the first restricted flow rate and the second restricted flow rate being increased at the patient ventilation interface based upon entrained gas through the entrainment port.

7. The apparatus of claim 1, wherein the controller regulates the valve to deliver a predefined measure of therapeutic breathing gas to a patient.

8. The apparatus of claim 7, wherein the predefined measure is one of a volume and a pressure.

9. The apparatus of claim 7, wherein the oscillations in the delivery of the therapeutic breathing gas to the patient are generated during only a portion of the selected patient expiratory or inspiratory phase.

10. The apparatus of claim 1, wherein the patient ventilation interface includes an entrainment port and a coupling of the patient ventilation interface.

11. The apparatus of claim 1, wherein the gas delivery circuit interconnecting the ventilator output port and the patient ventilation interface has a diameter less than 8 mm.

12. A patient ventilator secretion management system, comprising:
   a valve with an input in pneumatic communication with a therapeutic breathing gas source, the valve having variable positions each of which corresponds to a specific flow rate of gas being output from the valve;
   a patient ventilation interface in pneumatic communication with the valve over a gas delivery circuit;
   a first pressure sensor measuring a patient ventilation interface pressure, the patient ventilation interface being connectible to the first pressure sensor over a pressure sensor line;
   a second pressure sensor measuring a valve output pressure; and
   a controller in communication with the valve for regulating the position thereof, the controller sequentially switching the valve from one of the variable positions to another one of the variable positions to output a first range of fluctuating flow rates of gas for delivery to the patient ventilation interface during at least a selected one of the patient expiratory and inspiratory phases to induce oscillations in the flow of therapeutic breathing gas through the patient ventilation interface within a selected patient expiratory or inspiratory phase with an oscillation magnitude of the oscillations being controlled based on the measurement of the first pressure sensor.

13. The system of claim 12, wherein:
   the patient ventilation interface includes an entrainment port; and
   the first range of fluctuating flow rates from the valve is increased to a second range of fluctuating flow rates at a patient based upon entrained gas through the entrainment port.

14. The system of claim 12 wherein the gas delivery circuit has a diameter less than 8 mm.

15. The system of claim 12, wherein the controller is in communication with the flow sensor, and the patient inspiratory phase and the patient expiratory phase are detectable based upon measurements from the flow sensor.

16. The system of claim 12 wherein a rate of the sequential switching of the valve is defined by an oscillation frequency set by a user.

17. The system of claim 12, wherein one oscillation cycle is defined by a first flow rate corresponding to a first one of the variable positions of the valve, and a second flow rate corresponding to a second one of the variable positions of the valve.

18. The system of claim 17, wherein a difference between the first flow rate and the second flow rate defines the oscillation magnitude.

19. The system of claim 12, wherein the controller regulates the valve to deliver a predefined volume of therapeutic breathing gas to a patient.

20. A method for managing mucus secretion of a patient undergoing ventilation therapy with a ventilation apparatus, the method comprising:
   receiving on a controller data processing apparatus of the ventilation apparatus a value representing a therapeutic breathing gas delivery volume for delivery to the patient;
   receiving on the controller data processing apparatus at least one oscillation frequency value and at least one oscillation magnitude value;
   generating on the controller data processing apparatus a first valve positioning signal, the first valve positioning signal having a value corresponding to the at least one oscillating magnitude value and further based on a measurement of a patient ventilation interface pressure;
   applying the first valve positioning signal to a valve for positioning a valve element to deliver a first predetermined flow rate of therapeutic breathing gas to the patient at a first time instance within a selected patient expiratory or inspiratory phase;
   generating on the controller data processing apparatus a second valve positioning signal having a value corresponding to the at least one oscillating magnitude value and further based on the measurement of the patient ventilation interface pressure but different from the first valve positioning signal; and
   applying the second valve position signal to the valve for positioning the valve element to deliver a second predetermined flow rate of the therapeutic breathing gas to the patient at a second time instance, different from the first time instance, within the selected patient expiratory or inspiratory phase, the oscillation frequency value corresponding to a difference between the first time instance and the second time instance.

21. The method of claim 20, wherein a one of the oscillation frequency values and a one of the oscillation magnitude values are associated with a secretion mobilizing oscillation applied during an expiratory phase of the patient.

* * * * *